United States Patent [19]

Hinsch

[11] Patent Number: 4,557,264
[45] Date of Patent: Dec. 10, 1985

[54] SURGICAL FILAMENT FROM POLYPROPYLENE BLENDED WITH POLYETHYLENE

[75] Inventor: Bernhard Hinsch, Tangstedt, Fed. Rep. of Germany

[73] Assignee: Ethicon Inc., Somerville, N.J.

[21] Appl. No.: 597,857

[22] Filed: Apr. 9, 1984

[51] Int. Cl.[4] ............................................. A61I 17/00
[52] U.S. Cl. .................................. 128/335.5; 523/114; 428/364; 428/370
[58] Field of Search ............................. 128/335.5, 334; 523/114; 428/364, 370

[56] References Cited

U.S. PATENT DOCUMENTS 3,359,983 12/1967 Northey ............................ 128/335.5
3,630,205 12/1971 Listner .............................. 128/335.5

FOREIGN PATENT DOCUMENTS 2081585 2/1982 United Kingdom .

Primary Examiner—Jacqueline V. Howard
Attorney, Agent, or Firm—Charles J. Metz

[57] ABSTRACT

Surgical filaments such as sutures and ligatures are made from a blend of polypropylene and linear low density polyethylene.

5 Claims, 1 Drawing Figure

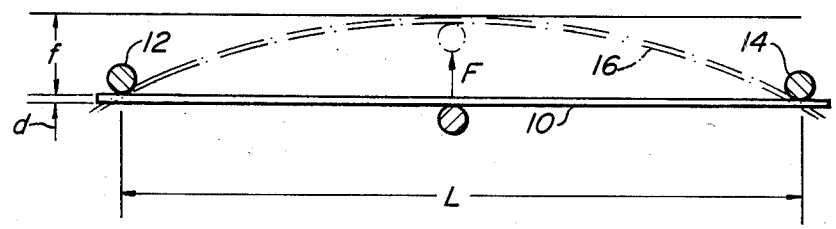

SURGICAL FILAMENT FROM POLYPROPYLENE BLENDED WITH POLYETHYLENE

This invention relates to surgical filaments made from a polypropylene-polyethylene blend.

BACKGROUND OF THE INVENTION

Surgical filaments such as sutures and ligatures have been made from a variety of different materials. Some of these are degraded in the tissue after a certain period. Others remain unchanged. Polypropylene sutures are preferred by the medical profession on account of their extreme inertness. The properties can be summarized as follows:
 a. they resist breakdown and do not promote infection;
 b. they maintain their in vivo tensile strength over extended periods;
 c. they show minimal reaction with body tissue;
 d. they have high tensile strength;
 e. they pass easily through body tissue; and
 f. they have good knot security.

The preferred polypropylene suture used in the medical profession today is described by Listner in U.S. Pat. No. 3,630,205.

The suture described by Listner has the following properties:

| Tensile Strength | 3.9–8.9 g/den |
| | about 320–730 N/mm$^2$ |
| Knot Strength | 3.3–7.9 g/den |
| | about 270–650 N/mm$^2$ |
| Break Elongation | 36–62% |
| Young's Modulus | 2200–3680 N/mm$^2$ |

As good as the current polypropylene sutures are, there is some room for improvement. In particular, it would be desirable to increase the compliance, limpness, or flexibility of polypropylene sutures in order to make them easier to tie and to improve their knot security. The problem is that previous efforts to accomplish this have occasioned a concomitant undesirable decrease in strength properties.

BRIEF DESCRIPTION OF THE DRAWING

FIG. 1 shows flexibility determination of the sutures according to the invention using an Instron tester equipped with a special adapter.

Recent developments have led to improved properties by using copolymers of propylene and ethylene (U.S. patent application Ser. No. 531,246). This material contains a few ethylene moieties in the polypropylene main chain. These moieties increase the flexibility.

In another approach it has been tried to add polyethylene to polypropylene because polyethylene has some of the desired properties. For these mixtures, conventional high density polyethylenes were used.

A description of commercially available polyethylene sutures is given in several patents (U.S. Pat. Nos. 3,105,493 and 3,359,983). They show good flexibility and limpness, but have poor in vivo strength retention and have in general tensile values which are about 50% lower than those found for polypropylene. In addition, these sutures show elongations which are more than twice as high as polypropylene. This is undesirable as it impedes tie down properties.

In sutures which are made of mixtures of polyethylene and polypropylene, the flexbility is indeed markedly increased. But at the same time some strength is lost, which is not acceptable for the surgeon. So these materials have never become important commercially.

Therefore, a new material was sought, which combines high compliance or flexibility, good knot security, and easy handling properties, along with the inertness of polypropylene. Polypropylene is a suture that is mainly used for applications where long-term stability and long-term wound support is required. Therefore, inertness, low tissue reaction, and above all, high level strength retention, are of extreme importance.

DETAILED DESCRIPTION OF THE INVENTIONS

According to this invention, mixtures of linear low density polyethylene (LLDPE) and polypropylene are used to make surgical filaments such as sutures and ligatures. It is surprising to note that when this special type of polyethylene is added in small amounts to polypropylene, the tensile strength is not lowered. It is significantly better than with pure polypropylene, but even more surprisingly, sharp decrease in stiffness or increase in compliance is observed. Break elongation is somewhat higher than for polypropylene, but far lower than for polyethylene. Interestingly enough, the Young's Modulus is also much lower for this new material than for either pure polypropylene or mixtures of polypropylene with conventional polyethylenes.

Linear low density polyethylene is a known material that is commercially available. It has a density of from 0.91 to 0.95 gram/cubic centimeter, and a melting point of 115°–130° C.

The polymer blend which was employed to extrude the suture consisted of high-molecular weight polypropylene which was preferably isotactic. Melt flow indexes (MFI 230/2.16) ranged from about 0.3 to about 11. Preferred are MFI values in the range of 0.3 to 3 in order to obtain high tensile strengths. The linear low density polyethylene used had melt flow indexes in the range of MFI (230/2.16) 0.3 to 70.

Polyethylene was used in concentrations of 0.1% to 25% by weight, preferably ranging from 1% to 16%. The polymer blend can contain colorants such as dyes or pigments, and stabilizers against heat, ultraviolet radiation and oxidation. Antistatic or antiblock additives, and lubricants may also be added, as well as radio-opaque components such as barium sulfate (in amounts up to about 60 percent, by weight, i.e., up to about 25 percent, by volume).

The sutures can be produced by extruding the polymer into filaments and subsequently orienting and annealing. Filament size can range from 1 denier for yarns up to size metric 5 (Ph. Eur.) (2 USP). Examples are given below. The sutures can then be attached to needles by common procedures. The filaments can also be braided, woven or knitted to form sutures or other devices for medical applications. The finished articles can be packed and sterilized for surgical applications.

EXAMPLE 1

The polymer blend contained 16% linear low density polyethylene of MFI (230/2.16) 1.0 and 84% polypropylene of MFI (230/2.16) 1.8, the percentages being based on weight of polyethylene plus polypropylene.

The material was processed as follows:

| Extrusion | | Orientation | |
|---|---|---|---|
| temperature | 240° C. | Draw Ratio | 8.0 |
| die diameter | 1 mm | oven temperature | 150° C. |
| pump pressure | 7 MPa | | |
| Annealing | | | |
| relaxation ratio | 0.82 | | |
| oven temperature | 150° C. | | |
| residence time | 40 sec. | | |

The resulting suture was 3.5 metric in size (#0 USP). The properties are shown below in Table I.

EXAMPLES 2 TO 5

Further samples were prepared as described above, from the same polyethylene and polypropylene. Conditions are summarized in Table III. They are compared to values for conventional polypropylene sutures which are commercially available (Table II).

TABLE I

Physical Properties of Sutures According to Invention

| Sample | Diameter, μm | knot intrinsic, N/mm² | straight intrinsic, N/mm² | break elongation, % | flexural modulus, N/mm² | PE content, % |
|---|---|---|---|---|---|---|
| 1 | 380 | 360 | 410 | 46 | 1600 | 16 |
| 2 | 304 | 405 | 430 | 30 | 2500 | 4 |
| 3 | 247 | 425 | 465 | 39 | 4480 | 8 |
| 4 | 173 | 510 | 550 | 33 | 4090 | 2 |
| 5 | 137 | 530 | 620 | 28 | 4320 | 12 |

TABLE II

Physical Properties of Commercially Available Polypropylene

| Sample | Diameter, μm | knot intrinsic, N/mm² | straight intrinsic, N/mm² | break elongation, % | flexural modulus, N/mm² | PE content, % |
|---|---|---|---|---|---|---|
| — | 375 | 340 | 360 | 31 | 2870 | — |
| — | 319 | 400 | 360 | 33 | 3840 | — |
| — | 245 | 420 | 390 | 26 | 10,100 | — |
| — | 182 | 410 | 420 | 30 | 13,100 | — |
| — | 139 | 440 | 490 | 29 | 14,800 | — |

The improved compliance, as illustrated by a reduction in flexural modulus, is striking.

TABLE III

| | Experimental Conditions | | | | |
|---|---|---|---|---|---|
| | Sample 1 | Sample 2 | Sample 3 | Sample 4 | Sample 5 |
| Extrusion | | | | | |
| temperature (°C.) | 240 | 250 | 250 | 250 | 240 |
| Die Diameter (mm) | 1 | 1 | 0.75 | 0.5 | 0.5 |
| Pump Pressure (MPa) | 7 | 7 | 7 | 7 | 7 |
| Orientation | | | | | |
| draw ratio | 8.0 | 9.0 | 9.0 | 9.0 | 8.5 |
| oven temperature (°C.) | 150 | 150 | 150 | 150 | 150 |
| Annealing | | | | | |
| relaxation ratio | 0.82 | 0.77 | 0.77 | 0.77 | 0.82 |
| oven temperature (°C.) | 150 | 130 | 130 | 130 | 150 |
| residence (sec.) | 40 | 40 | 70 | 70 | 40 |

Methods

Tensile strengths in straight pulls were tested on an Instron tester with a crosshead speed of 200 mm/min and a gauge 100 mm in length. Knot pull tensile strength was tested identically except that a single knot (Ph. Eur.) was thrown before the test.

Melt flow properties were assayed in an apparatus as described in DIN 53735 at 230° C. with a load of 21.6N (this corresponds to ASTM 1238, Cond. L). Flexibilities were determined with an Instron tester which was equipped with a special adapter. A piece of suture 10 was mounted between two pins (12 and 14) (FIG. 1).

The suture 10 was then bent, using a hook, to the position shown in dotted lines as 16. This hook was driven by the crosshead of the Instron. The bending force F, as measured by the Instron, was recorded as a function of the distance f. The flexural modulus E can be calculated by using the following equation:

$$E = \frac{F \cdot L^3 \cdot 3}{f \cdot d^4 \cdot \pi \cdot 2}$$

What is claimed is:

1. A drawn and oriented, strong and compliant, surgical filament comprising a physical blend of polypropylene and linear low density polyethylene, wherein the filament contains from about 0.1 to 25 weight percent linear low density polyethylene, based on weight of polyethylene plus polypropylene.

2. The surgical filament of claim 1 attached to a needle.

3. The surgical filament of claim 1 having the following properties:

| tensile strength | 350 to 900 N/mm² |
|---|---|
| intrinsic knot strength | 300 to 800 N/mm² |
| break elongation | 23 to 53 percent |
| flexural modulus | 1200 to 5000 N/mm² |

4. The surgical filament of claim 1, 2, or 3, wherein the filament contains from about 1 to 16 weight percent linear low density polyethylene, based on weight of polyethylene plus polypropylene.

5. The surgical filament of claim 1, 2, or 3 in sterile condition.

* * * * *